United States Patent
Shaw et al.

(10) Patent No.: US 6,171,329 B1
(45) Date of Patent: *Jan. 9, 2001

(54) SELF-EXPANDING DEFECT CLOSURE DEVICE AND METHOD OF MAKING AND USING

(75) Inventors: Edward E. Shaw; Robert C. Farnan, both of Flagstaff, AZ (US)

(73) Assignee: Gore Enterprise Holdings, Inc., Newark, DE (US)

( * ) Notice: Under 35 U.S.C. 154(b), the term of this patent shall be extended for 0 days.

This patent is subject to a terminal disclaimer.

(21) Appl. No.: 09/143,705

(22) Filed: Aug. 28, 1998

Related U.S. Application Data

(63) Continuation-in-part of application No. 08/995,097, filed on Dec. 19, 1994, now Pat. No. 6,080,182, which is a continuation-in-part of application No. 08/771,718, filed on Dec. 20, 1996, now Pat. No. 5,879,366.

(51) Int. Cl.[7] .................................................. A61B 17/00
(52) U.S. Cl. ............................ 606/213; 606/78; 606/151
(58) Field of Search ............................ 606/213, 78, 215, 606/151, 157, 158

(56) References Cited

U.S. PATENT DOCUMENTS

| | | |
|---|---|---|
| 3,124,136 | 3/1964 | Usher . |
| 3,874,388 | 4/1975 | King et al. . |
| 4,007,743 | 2/1977 | Blake . |
| 4,917,089 | 4/1990 | Sideris ............................ 606/215 |
| 4,994,077 | 2/1991 | Dobben ............................ 623/2 |
| 5,108,420 | 4/1992 | Marks ............................ 606/213 |
| 5,192,301 | 3/1993 | Kamiya et al. ............................ 606/213 |
| 5,334,217 | 8/1994 | Das ............................ 606/213 |
| 5,433,727 | 7/1995 | Sideris ............................ 606/213 |
| 5,536,274 | 7/1996 | Neuss ............................ 623/1 |
| 5,540,701 | 7/1996 | Sharkey et al. ............................ 606/153 |
| 5,607,465 | 3/1997 | Camilli ............................ 623/1 |
| 5,626,599 | 5/1997 | Bourne et al. ............................ 606/194 |
| 5,879,366 | 3/1999 | Shaw et al. ............................ 606/213 |

FOREIGN PATENT DOCUMENTS

| | | |
|---|---|---|
| 2 269 321 | 2/1994 | (GB) . |
| 1468511 A1 | 2/1987 | (SU) . |
| 98/08462 | 3/1988 | (WO) . |
| 90/14796 | 12/1990 | (WO) . |
| 94/07560 | 4/1994 | (WO) . |
| 95/27448 | 10/1995 | (WO) . |
| 97/28744 | 8/1997 | (WO) . |
| 97/41779 | 11/1997 | (WO) . |

OTHER PUBLICATIONS

Article—A Small Interventional Device to Occlude Persistently Patent Ductus Arteriousus in Neonates: Evaluation in Piglets. *J. Am Coll Cardiol 1996; 28:1024–30.*

*Primary Examiner*—Gary Jackson
(74) *Attorney, Agent, or Firm*—David J. Johns

(57) ABSTRACT

The present invention relates to a self-expanding device for sealing a defect in a wall, such as a septal defect. The device of the present invention has a helical shaped periphery formed from an elastic wire and at least one eyelet. The eyelet has a non-circular ("asymmetric") shape which allows the eyelet to slide along a guiding mandrel. The non-circular shaped eyelet and mandrel prevent rotation of the eyelet relative to the mandrel thereby ensuring a consistent deployed shape. The present invention also incorporates a self-articulating catheter tip which can be bent to a variety of angles to enhance the ease of delivery. The tip is articulated by varying the position of the closure device within the articulated portion of the catheter.

30 Claims, 15 Drawing Sheets

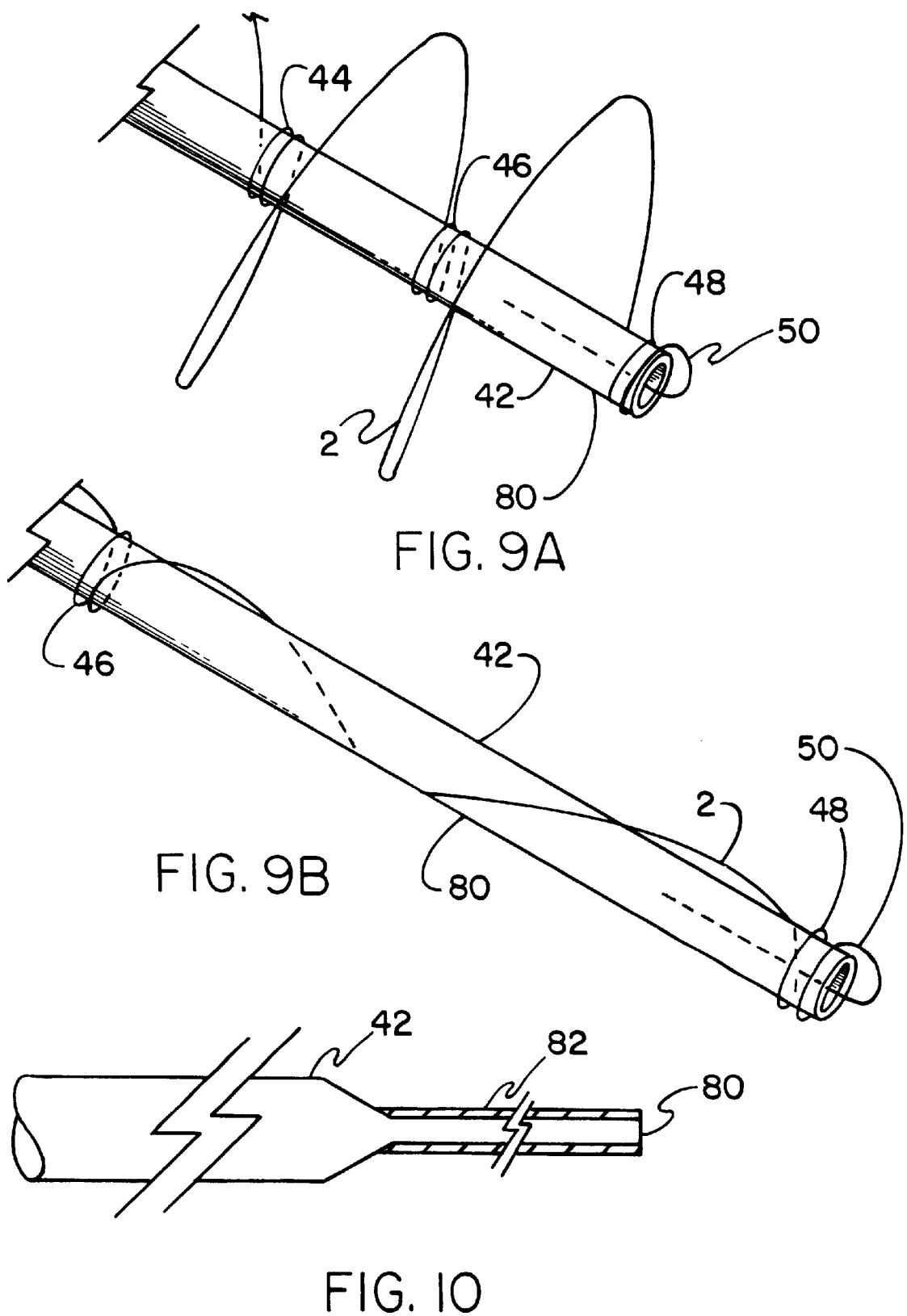

SELF-EXPANDING DEFECT CLOSURE DEVICE AND METHOD OF MAKING AND USING

RELATED APPLICATIONS

The present application is a continuation-in-part of U.S. patent application Ser. No. 08/995,097, filed Dec. 19, 1997, now U.S. Pat. No. 6,080,182, which is a continuation-in-part of U.S. patent application Ser. No. 08/771,718, filed Dec. 20, 1996, now U.S. Pat. No. 5,879,366.

FIELD OF THE INVENTION

The present invention relates to closure devices, their manufacture and use to occlude a defect in a tissue or muscle of a animal, such as a human being, or a defect in a wall of a structure, such as a container or filter. More specifically, the present invention relates to a self-expanding closure device having a membrane that is supported by a structure having elastic properties, which is capable of being compacted and inserted through a defect, and thereafter returned to an enlarged configuration to cover or seal the defect.

BACKGROUND OF THE INVENTION

A wall defect is generally a hole in the wall of the tissue of an animal, such as humans, or a hole in the wall of a container, tank, bag filter, or planar filter, tent, inflatable device, etc. In muscles or tissues of animals, repairs have been accomplished by inserting an occlusion or septal closure device into the aperture or defect. Such devices include those taught by U.S. Pat. Nos. 5,334,217 to Das and 5,108,420 to Marks.

The Das patent describes a septal defect closure device, its use and method of assembly, where individual disks of a thin flexible material are supported by a super-elastic material and are used to occlude a wall defect. The disks are conjointly attached to one another at the center of the disk. The thin flexible material used in the Das patent can include nylon, polyester, polypropylene and polytetrafluoroethylene (PTFE) polymers. The super-elastic material is a NiTi alloy (or "nitinol".)

The super-elastic material of the Das patent is formed into a frame having several legs and can assume geometrical configurations such as triangles, hexagons, circles, and stars. A membrane is wrapped around the legs of the frame. The loops between adjacent legs bias the legs outwardly, to form a concave membrane surface, which is maintained in a highly tensioned fashion.

The Marks patent describes an occlusion device that can be transported via a catheter in a compressed state. Once through an aperture to be occluded, the device is released and wires supporting two membranes are positioned on each side of the aperture. A domed or umbrella shaped configuration is formed and the support wires urge the membranes towards one another and the wall where the aperture is located.

These prior devices have numerous drawbacks. The support frames of the Das patent include resilient wire loops where leg ends of the frame meet and are attached to one another. The loops generally extend beyond the periphery of the membrane and can irritate or damage adjacent muscle or tissue.

Similarly, the exposed wires of the Marks device act as an irritant to tissue or muscle adjacent the aperture or septum. Here the bare sharp ends of the wire structure can further cause tissue erosion.

The Das and Marks patent devices use a membrane of conventional thickness that when folded over a wire add undesired thickness to the device. Additionally, the patents rely on peripheral membrane support which leaves the central occlusion covering portion of the membrane vulnerable.

In the Das patent design, each leg is provided with a bend at the middle of its length. This bend may tend to fold the device when the frame is sitting against a very flexible tissue and the membrane is pressurized by the blood. This may be the potential mechanism of failure as reported in Agarwal, S. K., Ghosh, P. K. and Mittal, P. K., "Failure of Devices Used for Closure of Atrial Septal Defects: Mechanisms and Management," *The Journal of Thoracic and Cardiovascular Surgery*, Vol. 112, No. 1, 1996.

Finally, it is believed that none of the previously available devices have provided a sufficiently small enough insertion diameter and/or collapsed flexibility. This limitation has restricted the utility and ease of use of such devices.

Thus, in view of the above, it is desirable to provide a closure device that eliminates or significantly minimizes the traumatizing effect of existing closure devices. Further, it is desirable to provide such a device to be stable under physiological loading conditions when situated against the anatomical tissue structure. It is additionally desirable to provide a defect closure device that is collapsible or compressible so that it may fit into a 9F (9 French), preferably 5F or 4F or smaller catheter for deployment in a defect.

These drawbacks and disadvantages of the prior devices have been addressed and overcome by the inventions described in the two co-pending patent applications. These prior inventive devices employ unique nitinol frames combined with thin expanded PTFE membranes to create defect closure devices that function better than any previous defect closure devices. Of particular benefit of these devices is the fact that they are capable of being compacted into very small delivery tools and then deploy to fully operational diameters. Additionally, unlike some previous defect closure devices, these inventive devices provide excellent protection of tissue from damage by the frame, which is protected under the expanded PTFE cover. Further, these inventive devices also are capable of being relatively easily withdrawn remotely from the defect site in the case they need to be retrieved.

Despite the excellent properties of the defect closure devices disclosed in the parent applications, on-going development work has revealed that further improvements may be possible on these devices. First, it has been discovered that with devices with helical frames the device must be carefully deployed to assure that the helical frame initially starts to expand with the correct spiral. If the helix starts unwrapping in the wrong direction, the operator must withdraw the device back into the delivery tool and attempt deployment a second time to assure that the device expands correctly. Accordingly, a frame which consistently deploys with the correct bias in the helical frame is believed desirable.

Second, the use of the parent devices within tortuous anatomy generally requires the use of separate guidewire catheters or similar devices to help negotiate the device delivery apparatus to the deployment site. This requires both the use of additional equipment and often taxes space limitations at a surgical site. Thus, it is further believed desirable to incorporate a simpler and more compact system that can assist in negotiating the deployment apparatus to the defect site.

SUMMARY OF THE INVENTION

The present invention provides significant improvements to deployment and use of the self-expanding defect closure device described in the co-pending parent applications. The defect closure device of the present invention comprises a helical shape periphery supporting a membrane. The helical shape periphery is formed from an elastic wire. Specific improvements have been made to the elastic wire frame and the delivery apparatus to assure consistent correct delivery of the device at the operative site. Additionally, the deployment apparatus has been modified to aid in the negotiation of the device to the site of deployment.

Specifically, the wire frame now includes at least one eyelet having a non-circular or "asymmetric" shape. A guiding mandrel is similarly shaped to have a complimentary non-circular or asymmetric shape which allows the eyelet to slide linearly along the mandrel. The asymmetric shapes of the wire eyelet and the guiding mandrel prevent rotation of the eyelet relative to the mandrel. This anti-rotation feature of the present invention provides a bias or constraint to the formed elastic support, particularly for a helix shaped support. Without this applied bias, a helical wire might assume various deployed shapes. The addition of the bias means of the present invention insures a consistent deployed state or configuration.

Additionally, to deliver and place a septal defect closure device intravenously, the delivery catheter often must be guided through a tortuous path. It is thus another aspect of the present invention to provide a self-articulating catheter tip which facilitates and enhances the ease of delivery. To this end, the catheter is provided with a hooked end adapted to assist in guiding the catheter tube through passageways in a body, much in the same way that a guidewire catheter can be "snaked" through tortuous anatomy using its hooked end to "steer" the guidewire into place.

In the present invention, the hooked tip is integrally incorporated into the deployment apparatus to assist in steering the deployment apparatus to the deployment site. Once in place, however, the deployment apparatus is adapted to eliminate the hooked tip to provide accurate defect closure device placement. This is accomplished by providing a self-articulating catheter tip that can be bent to a variety of angles by advancing or retracting the closure device from the proximal end of the delivery catheter. In other words, as the defect closure device is advanced through the tip of the catheter, the tip will straighten out to provide linear deployment of the defect closure device. Thus, the catheter tip is adapted to assume at least two different positions, an angular or bent guiding position and a straightened device deployment position. The catheter tip actuates from the guiding position to the device deployment position when the defect closure device is moved through the distal tip of the catheter. To accomplish this, the catheter tube comprises a flexible material adapted both to maintain a bent orientation while being negotiated into position and to flex so as to straighten the hooked end when a device is deployed through the tube.

These and other aspects and advantages will become more apparent when considered with the following detailed description, drawings and appended claims.

BRIEF DESCRIPTION OF THE DRAWINGS

FIGS. 9(A) and (B) show the helical shaped wire, the integral biasing anti-rotation feature, with the wire in relaxed and linearly constrained states.

FIG. 10 shows a low friction coating on the guiding mandrel.

DETAILED DESCRIPTION OF THE INVENTION

Figure 1A:
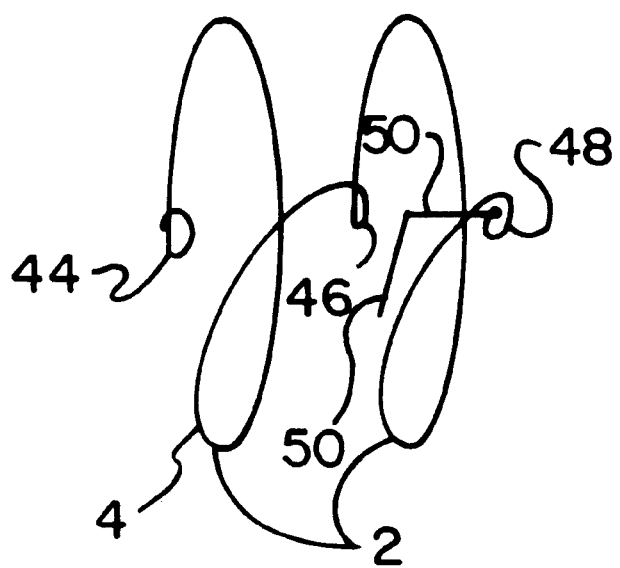
FIG. 1(A) shows the helical shaped elastic wire of the present invention.

The defect closure devices of the present invention are composite assemblies of support structures and membranes. For biological applications, the membranes may be made from biocompatible materials such as expanded polytetrafluoroethylene (PTFE). Such membranes block the defect, for example a septal defect, in an animal and occlude the blood flow. This device can also be used to repair a variety of wall defects, either by remote or direct deployment.

A wall defect can be remotely repaired in a fluid containing vessel without draining the fluid. Other wall defects in contact with hazardous materials or environments can be remotely repaired. In addition, those defects where access is limited due to confined spaces or submersion, can also be remotely repaired. Direct deployment can be used to repair wall defects in those cases where access is non-restricted or limited by the immediate environment.

The supporting wire structures that are used in the devices according to the present invention have elastic properties that allow for them to be collapsed for catheter based delivery or thoracoscopic delivery, and self-expand to a "memory" induced configuration once positioned in a wall defect. The elastic wire may be a spring wire, or a shape memory NiTi alloy wire or a super-elastic NiTi alloy wire (generally referred to herein as "nitinol"). Upon deployment, the wire structure resumes its deployed shape without permanent deformation.

The supporting structures of the present invention are formed from elastic wire materials that have diameters between about 0.12 and 0.4 mm. In a preferred embodiment of the present invention, the wire is about 0.3 mm in diameter and formed from nitinol metal.

The membrane that is used in the defect closure devices to occlude the flow of blood can be manufactured from a variety of materials, such as DACRON® polyester, polyethylene, polypropylene, fluoropolymers, polyurethane foamed films, silicone, nylon, silk, thin sheets of superelastic materials, woven materials, polyethylene terephthalate (PET), collagen, pericardium tissue or any other biocompatible material. In one embodiment of the present invention, the membrane material is a fluoropolymer, in particular, expanded polytetrafluoroethylene (PTFE) having a node-fibril structure, such as that described in U.S. Pat Nos. 3,953,566, 4,962,153, 4,096,227, 4,187,390, and 4,902,423, all incorporated by reference. The membrane used in the present invention is manufactured from thin films of expanded PTFE that are each approximately 0.0025 to 0.025 mm thick. Thus, the films could be about 0.0025, 0.005, 0.0075, 0.01, 0.0125, 0.015, 0.175, 0.02, 0.0225 and 0.025 mm or more thick.

From 1 to about 200 plys (layers) of expanded PTFE film are stacked up and laminated to one another to obtain a membrane with the desired mechanical and structural properties. An even number of layers are preferably stacked together (e.g., 2, 4, 6, 8, 10, etc.), with approximately 2 to 20 layers being desirable. Cross-lamination occurs by placing superimposed sheets on one another such that the film drawing direction, or stretching direction, of each sheet is angularly offset by angles between 0 and 180 degrees from adjacent layers or plies. Because the base expanded PTFE is thin, as thin as about 0.0025 mm or less in thickness, superimposed films can be rotated relative to one another to improve the mechanical properties of the membrane. In one embodiment of the present invention the membrane is manufactured by laminating together 8 plies of expanded PTFE film, each film ply being about 0.0125 mm thick. In another embodiment of the present invention the membrane is manufactured by laminating together 4 plies of expanded PTFE film, each film ply being about 0.0125 mm thick. The laminated expanded PTFE sheets are then sintered together at temperatures of about 370° C., for about 15 minutes under vacuum to adhere the film layers to one another. The resultant 8 ply laminate structure is typically about 0.04 mm thick.

The invention will now be described by reference to the figures and non-limiting embodiments. One embodiment for closing an aperture or defect according to the present invention is a helical design. As shown in FIG. 1(A), a helical shaped wire frame 2 for a defect closure device is prepared from a super-elastic wire material 4. A wire 4 of nitinol is fixtured in a jig (not shown) into a shape of a helix 2, eyelets 44, 46, 48, and latching and securing portions 50. As is explained in greater detail below, one or more of the eyelets 44, 46, and 48 are preferably formed in a non-circular shape.

The helix 2 shape can include any shape that forms at least a partial outer periphery and has a longitudinal length. For example, a helical shape can include a coil with varying or consistent diameters and angles. The outer periphery of the helical shape can include straight as well as arced segments. Each helix shape 2 is preferably formed from a single wire that is configured to be helical in shape, although multiple wires may be used.

The helical shaped wire 2 is constrained in a jig (not shown) and the combination is placed into an oven, heated for at least two minutes, up to about one-half hour, at about 400° to 600° C., e.g., about 500° C. The helical shaped wire 2 is cooled by immersing in approximately 25° C. water, and removed from the restraining jig. As the result of the 500° C., 30 minute heat treatment, the nitinol wire 4 obtains a memory induced configuration, which in this case is the shape of a helix. The helical shaped wire 2 exhibits superelastic properties, which act to return the wire to the helical shape even after extreme deformation, such as the straightened orientation shown in FIGS. 4(A) through 4(C).

Figure 1B:
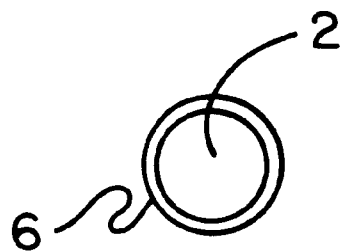
FIG. 1(B) shows a cross section of the helical shaped wire with the bonding adhesive on the outer diameter of the wire.
Figure 1C:
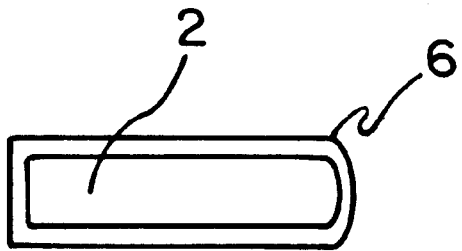
FIG. 1(C) shows a cross section of the helical shaped wire with the bonding adhesive on the perimeter of a non-circular wire or ribbon.

As shown in cross section FIG. 1(B), the helical shaped wire 2 is coated with a bonding agent 6, for example fluorinated ethylene propylene (FEP) or other suitable adhesive. The adhesive may be applied through contact coating, powder coating, dip coating, spray coating, or any other appropriate means. As shown in FIG. 1(C), the cross section of the wire 2 is not limited to circular forms and may include rectangular shaped ribbons, square forms, other polygones, or other shapes.

In a preferred embodiment, the FEP adhesive is applied by electrostatic powder coating per the following process. The formed helical shaped wire is first pre-cleaned with isopropyl alcohol and de-ionized water. The formed wire is then placed onto a spreading and holding fixture to avoid wire to wire contact in the formed periphery area. The fixtured wire is then grounded and placed, for approximately 10 seconds, into the electrostatically charged FEP cloud. The FEP powder can be procured from Daikin Industries, Ltd., Osaka, Japan, as part number NCX-1. The FEP powder is then removed from the eyelets 44, 46, 48 and the latching and securing portions 50, by brushing or by the use of vacuum. The FEP coated wire frame and support fixture is then placed into a convection oven and heated to approximately 330° C. for approximately 1 to 2 minutes, in order to melt and adhere the FEP powder to the formed wire. The FEP coating can also be applied by dipping, spraying, laminating between sheets, wrapping FEP film, fitting FEP tubes over the formed wires, or any other means. If more than one wire is used to form the helical shape the two ends of the formed wire are attached together at a termination point, by welding, by crimping a sleeve onto the wire ends, or any other means.

Figure 2A:
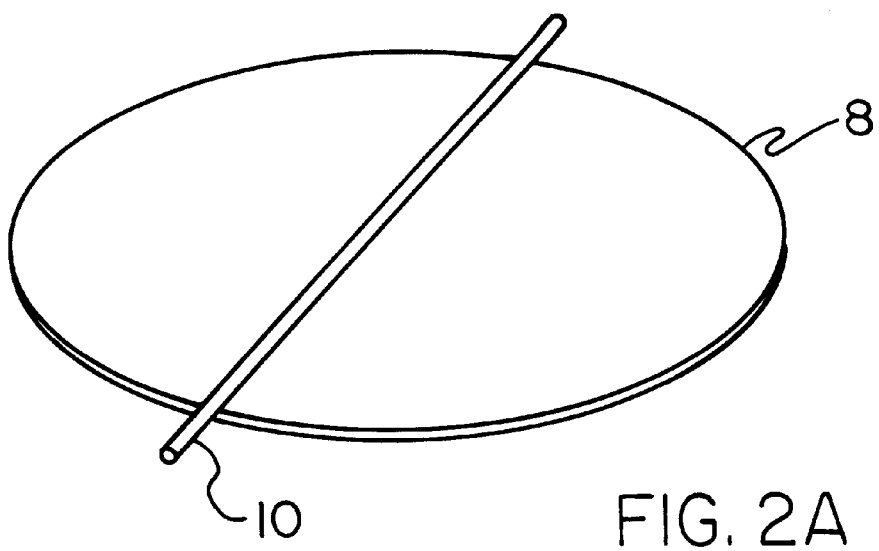
FIGS. 2(A) through (C) show a multi-ply laminate being folded over a heat resistant tube during the helical device fabrication process.

FIG. 2(A) shows a multi-ply laminate 8 prepared from, for example, four film layers (plies) of expanded PTFE. The film layers are placed onto a porous vacuum chuck (not shown) with each film layer being rotated about 90 degrees relative to one another. The four ply laminate 8 can be disk shaped or any other shape. A high temperature tube 10 is placed on the center line of the four ply laminate 8.

Figure 2B:
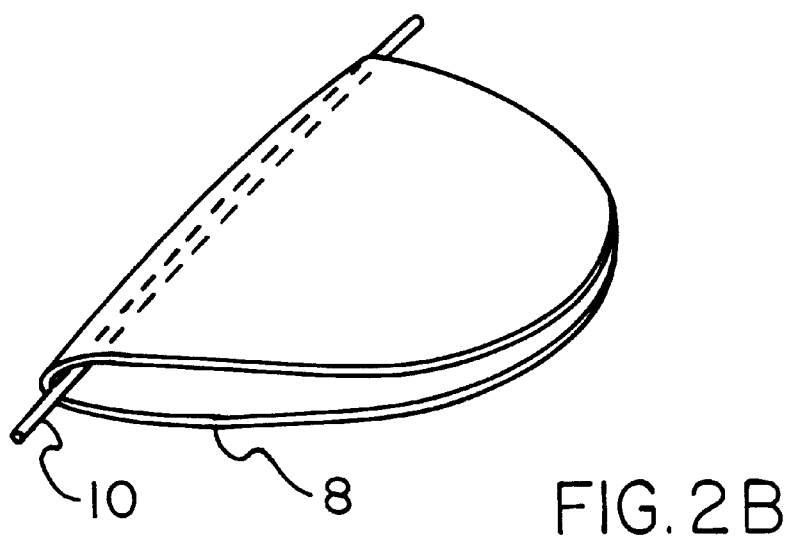

FIG. 2(B) shows the multi-ply laminate 8 being folded over the high temperature tube 10, forming a folded laminate which surrounds the tube.

Figure 2C:
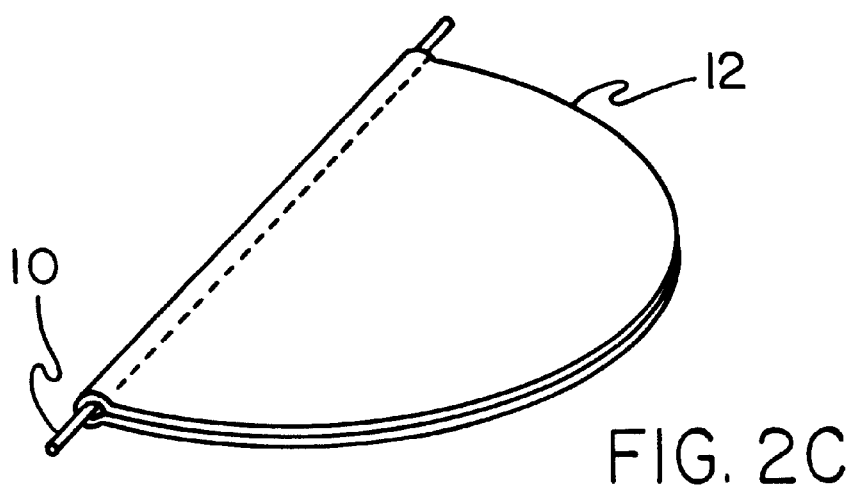

FIG. 2(C) shows the folded laminate. Since the four ply laminate has been folded once, the membrane 12 now has formed an eight ply laminate. This laminate assembly, with the embedded tube, is capped with a KAPTON® sheet and placed into a sintering press. The edges of the laminate are constrained, vacuum is applied to the assembly through a porous chuck, and the assembly heated to sintering temperatures. The times and temperatures for this sintering process are as previously described. The sintered assembly is cooled and the KAPTON® sheet is removed and discarded.

Figure 2D:
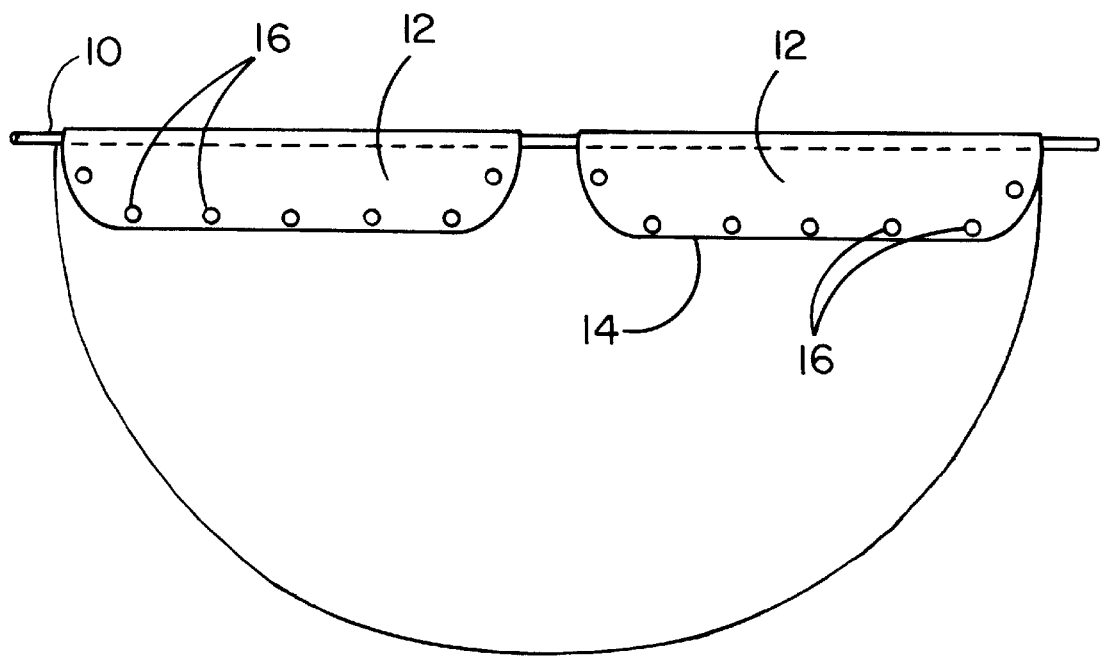
FIGS. 2(D) and (E) shows the final laminate sheet, cutting pattern and guiding mandrel hole pattern for the helical closure device.

FIG. 2(D) shows the laminate assembly, or membrane 12, high temperature tube 10, outline cutting 14 and mandrel hole patterns 16. The outline and mandrel holes are cut by laser, steel rule die, or any other means.

Figure 2E:
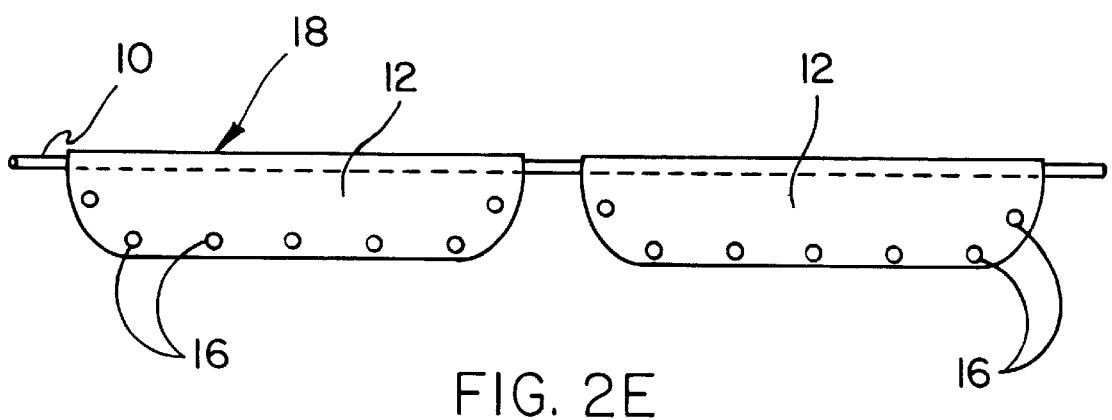

As shown in FIG. 2(E), after the cutting operation, a laminated assembly 18 is formed having membranes 12, mandrel holes 16 and a heat resistant tube 10.

Figure 3A:
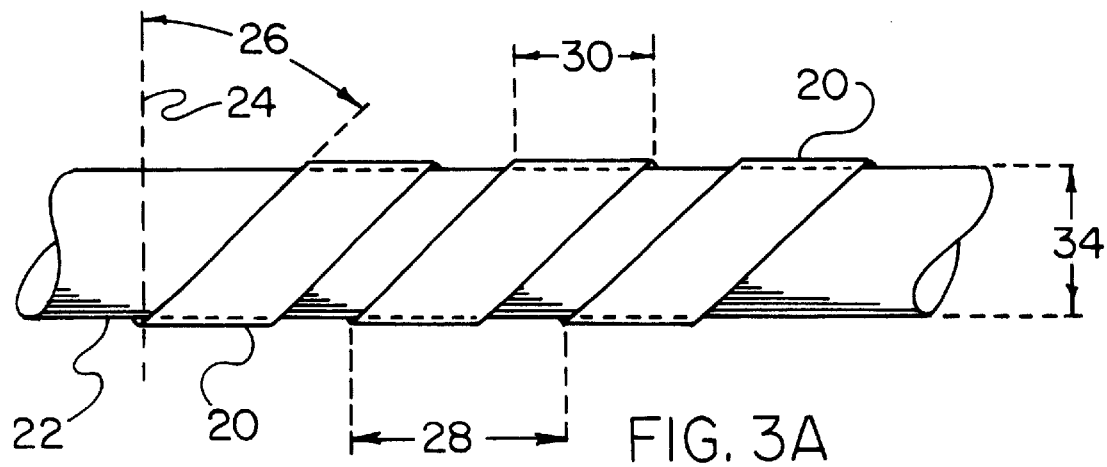
FIGS. 3(A) through (C) show an alternate wrapped film tube process for fabricating the multi-ply film laminate.
Figure 3B:
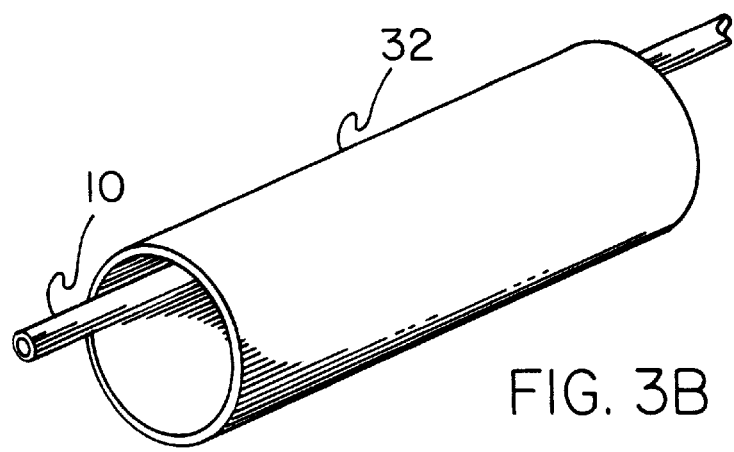
Figure 3C:
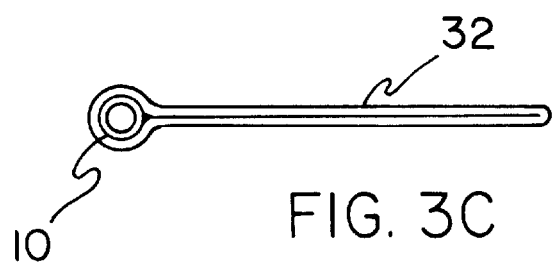

In a preferred or alternate method, the cross laminated membranes may be manufactured by cross wrapping film around a mandrel, thereby creating a cross ply laminated film tube. As shown in FIG. 3(A), the film 20, as previously described, is wrapped around a mandrel 22. The film 20 is wrapped at an angle 26, referenced from a vertical or shortest circumference line 24 about the mandrel. A clockwise angle from the vertical reference is described as positive angle while a counterclockwise angle is described as a negative angle. Shown is a preferred angle 26 of positive 47 degrees from vertical. The film 20 is preferably wrapped with a pitch 28 of approximately 1.75" (44.45 mm), the film width 30 is preferably about 1.0" (25.4 mm) and the mandrel diameter 34 is preferably about 1.0" (25.4 mm). The film is wrapped accordingly to an approximate 24" (~610.0 mm) length, traversing from left to right, completing one pass. The second pass, traversing from right to left maintains the same pitch 28 and film width 30, but the wrap angle 26 is changed to negative 47 degrees from vertical. As shown in FIG. 3(B), a total of eight passes are used to produce a cross ply laminated film tube 32. While still on the wrapping mandrel, the film laminate is sintered at approximately 370° C. for approximately 45 minutes. The sintered film tube is then removed from the wrapping mandrel. The heat resistant tube 10 can then be inserted into the tube lumen as shown. This assembly, with the embedded tube, is then capped with a KAPTON® sheet and placed into a sintering press. The edges of the laminate are constrained, vacuum is applied to the assembly through a porous chuck, and the assembly heated to sintering temperatures. The times and temperatures for this sintering process are as previously described. The sintered assembly is cooled and the KAPTON® sheet is removed and discarded. Shown in FIG. 3(C) is an end view of the laminated assembly, showing the heat resistant tube 10 and the folded and laminated film tube 32. This assembly can then be fixtured onto a laser chuck to allow the cutting of the mandrel holes 16 (FIG. 2(D)) and device outline 14 (FIG. 2(D)). As previously shown in FIG. 2(E), after the cutting operation, a laminated assembly 18 is formed having membranes 12, mandrel holes 16 and a heat resistant tube 10.

The helical wire 2 (FIG. 1(B)), with the FEP coating 6 (FIG. 1(B)), is then tensioned into an approximate linear shape and inserted into the high temperature tube 10, such as one constructed from stainless steel. The high temperature tube 10 is removed from the laminated assembly 18, leaving the FEP coated wire captured within the laminated assembly. The latch and securing portion of the helical formed wire is threaded through the pre-cut mandrel holes to temporarily hold the device in the approximate deployed or expanded state. By threading the latch and securing portion of the helical formed wire through the pre-cut guiding mandrel holes, the central edges of the seal members or membranes are forced to radially converge in upon themselves, thus assuming the final deployed configuration. The device is then air heated at 330° C. for about 15 minutes causing the FEP coating on the wire to bond to the expanded PTFE laminate. The device is then allowed to cool. The resulting device, when linearly tensioned, is depicted in FIG. 4(A).

Figure 4A:
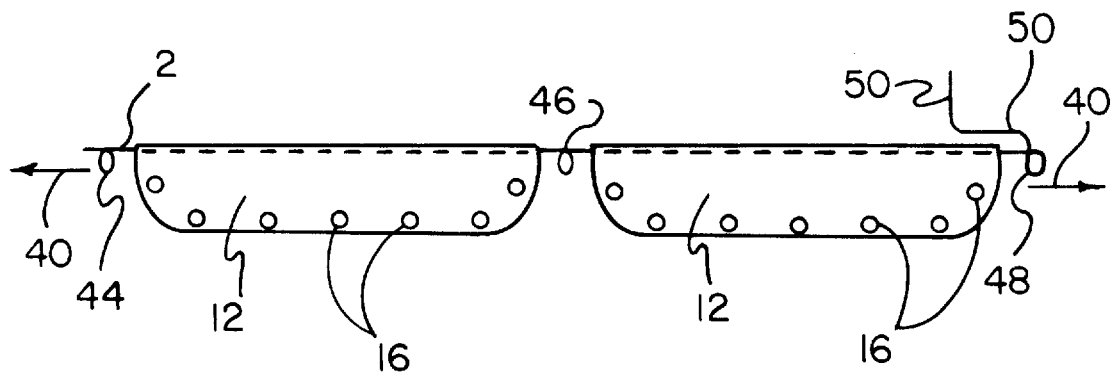
FIGS. 4(A) through (C) show the process for threading the guiding mandrel through the eyelets and pre-cut mandrel holes.
Figure 4B:
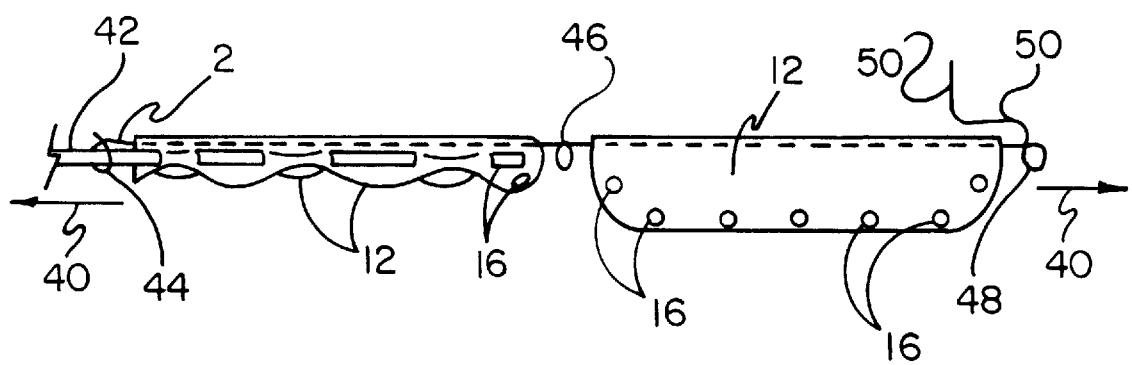

As shown in FIG. 4(A), the device is linearly tensioned by applying loads 40. The helical shaped wire 2 has been formed as previously described. Formed into the wire 2 is a proximal eyelet 44, an intermediate eyelet 46, a distal eyelet 48 and a latching and securing means 50. The sealing membranes 12 have pre-cut mandrel holes 16. As shown in FIG. 4(B) a guiding mandrel 42 is threaded through the proximal eyelet 44 and sequentially through the pre-cut mandrel holes 16. The guiding or gathering mandrel forces the pre-cut holes to be approximately aligned to a common axis thus gathering the inner edges of the sealing membranes. The guiding mandrel 42 is essentially straight or nearly linear, thus the sealing membranes 12 should be folded or compressed to feed the guiding mandrel sequentially through the pre-cut holes 16.

The guiding mandrel is essentially tubular and can have inner diameters ranging from about 0.005" to 0.300" (0.13 mm to 7.62 mm), with a preferred range of about 0.031" to 0.033" (0.79 mm to 0.83 mm). The guiding mandrel can have an outer diameter ranging from about 0.007" to 0.500" (0.18 mm to 12.7 mm), with a preferred range of about 0.039" to 0.041" (0.99 mm to 1.04 mm).

The guiding mandrel can be fabricated from any suitable bio-compatible material including polymers or metals. A preferred guiding mandrel material is nitinol, procured from Memry Corp., Melno Park, Calif. The guiding mandrel can be surface treated or coated to enhance the material's bio-compatibility or alter or enhance the surface friction.

Figure 4C:
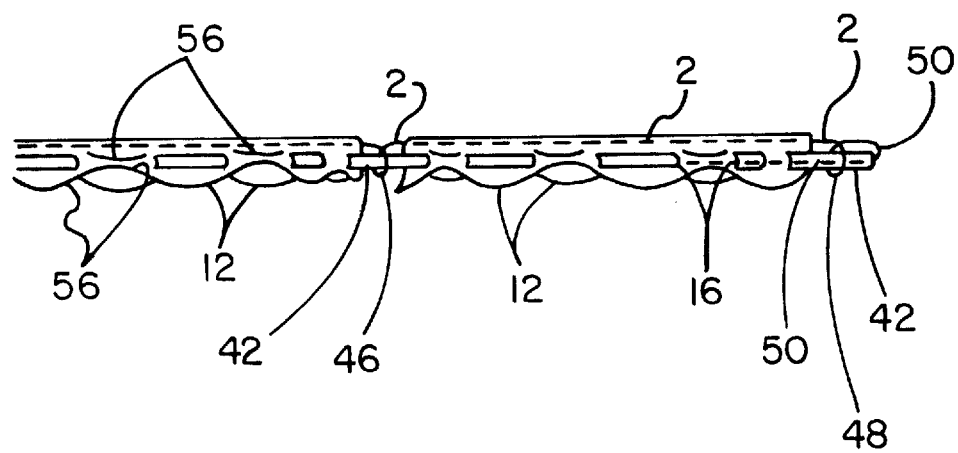

As shown in FIG. 4(C), the guiding mandrel 42 is further threaded through the intermediate eyelet 46, through the remaining pre cut holes 16 and through the distal eyelet 48. The sealing membranes 12 are typically folded or wrinkled as depicted by wrinkles 56. The latching and securing means 50, which was pre formed into the helical shaped wire 2, is resiliently deformed and positioned into the open distal end of the guiding mandrel 42. The helical wire is then tensioned into a linear shape by sliding the proximal eyelet along the guiding mandrel away from the distal end of the guiding mandrel. The device is then loaded into a delivery catheter.

Figures 5A, 5B:
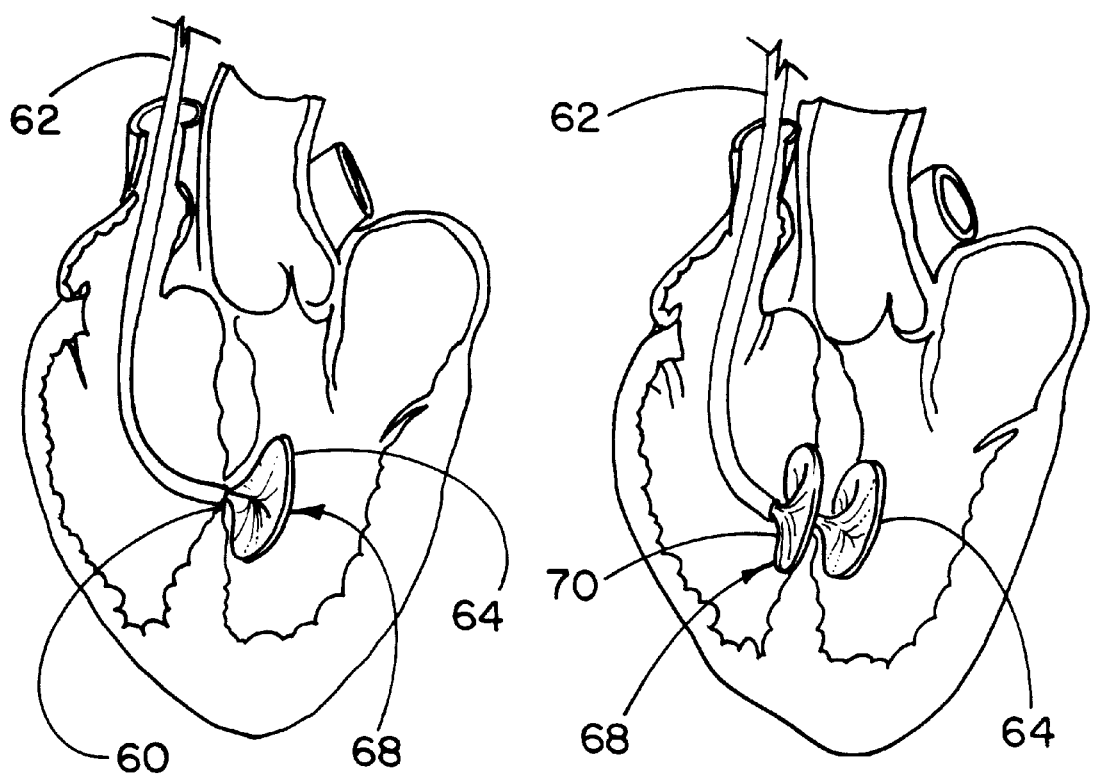
FIGS. 5(A) through (C) show a helical defect closure device according to the present invention being positioned and deployed in a heart defect.
Figure 5C:
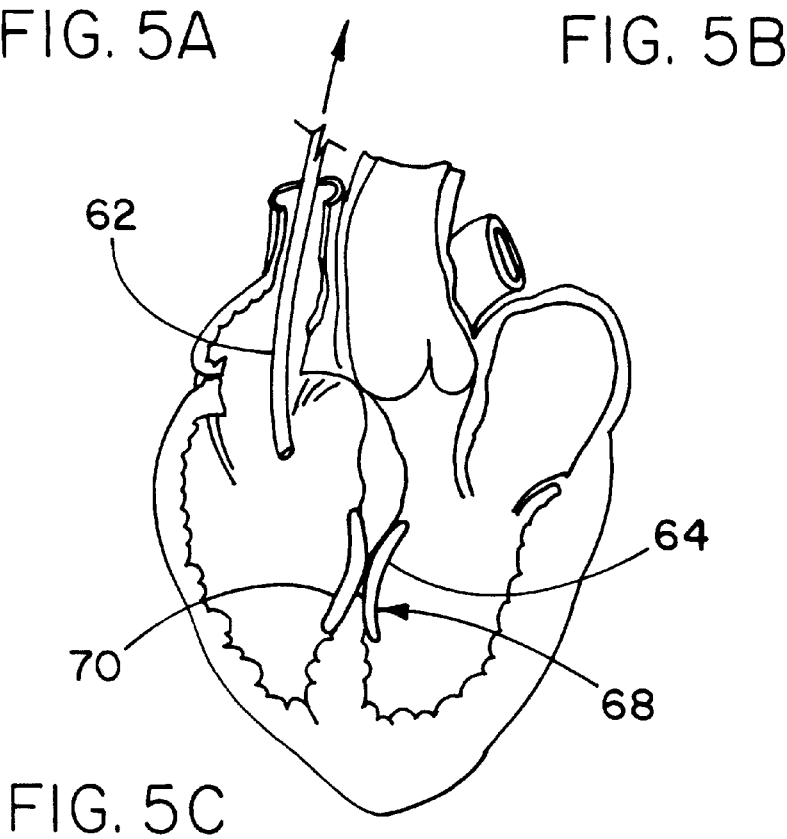
Figure 5D:
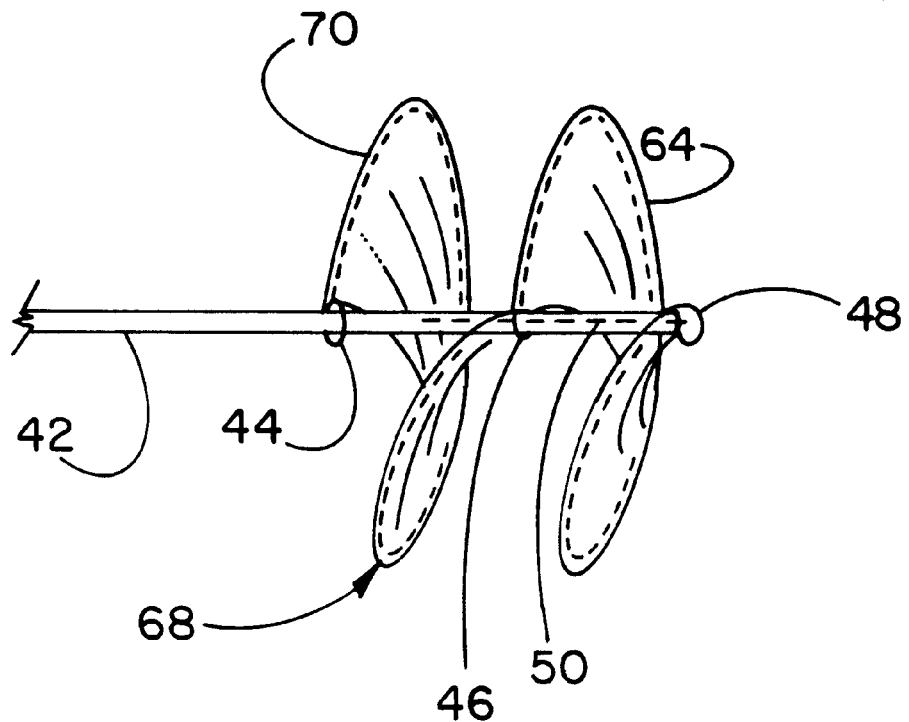
FIGS. 5(D) and (E) show a helical defect closure device according to the present invention with and integral latch and sealing membrane to sealing membrane securing means.
Figure 5E:
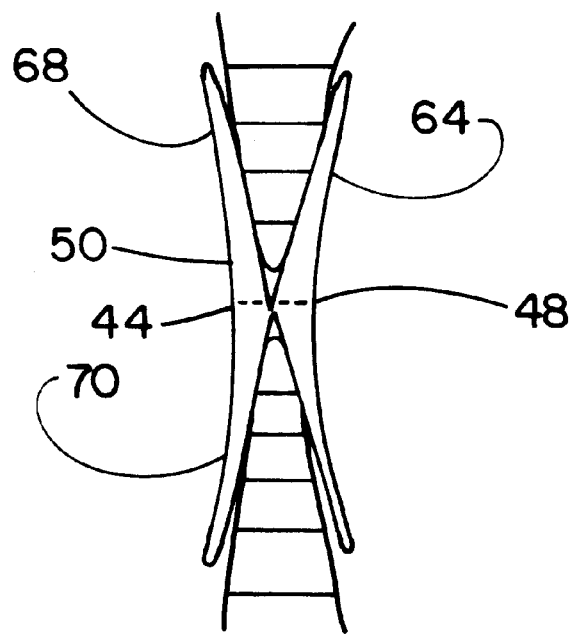

The general deployment of the completed helical closure device is shown in FIGS. 5(A)–(C). The delivery catheter 62 is initially positioned through a wall defect 60 in a heart. As shown in FIG. 5(A) the distal sealing membrane 64 of the helical closure device 68 is forced out of the delivery catheter 62, allowing the distal side 64 to expand to the deployed shape. As shown in FIG. 5(B), the catheter 62 is withdrawn out of the wall defect, the closure device is forced further out of the catheter, allowing the proximal sealing membrane 70 to expand to the deployed shape. As shown in FIG. 5(C), when the guiding mandrel and catheter 62 are withdrawn, the latch and securing portion of the formed wire captures and secures the distal eyelet to the proximal eyelet, thereby securing the distal sealing membrane 64 to the proximal sealing membrane 70. The latching and securing means is further clarified in FIGS. 5(D) and (E). As shown in FIG. 5D, the latching and securing means 50 is constrained within the inner lumen of the guiding mandrel 42. The guiding mandrel is also threaded through the three eyelets 44, 46 and 48 and through the pre-cut mandrel holes. When the proximal eyelet 44 is forced towards or forced to be in close proximity to the distal eyelet 48, the latching means will protrude through the proximal eyelet 44, the medial eyelet 46, and the distal eyelet 48. As shown in FIG. 5(E), when the guiding mandrel 42 is withdrawn, the latching and securing means 50 will be positioned within the three eyelets and will return to the deployed state on the proximal side of the closure device 68. Thus by securing the eyelets together, the proximal sealing membrane 70 is secured to the distal sealing membrane 64, completing the closure of the wall defect.

Figure 6A:
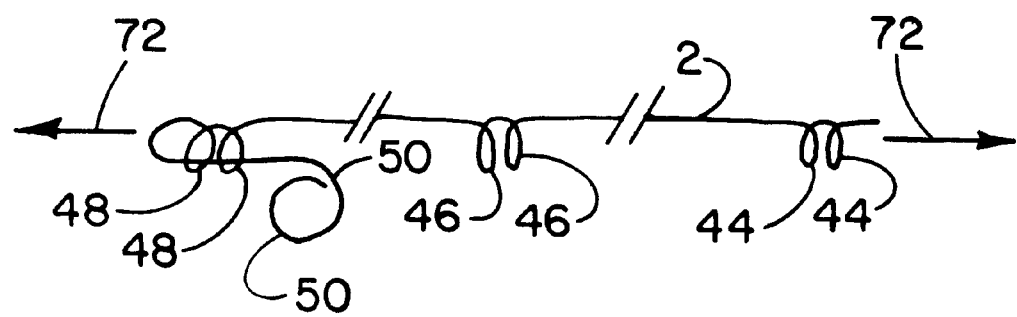
FIGS. 6(A) and (B) show detailed shapes of the helical formed wire in a linearly constrained and in a unconstrained state.

As shown in FIG. 6(A), the helical shaped wire can have more than one loop forming any eyelet. For example, the proximal eyelet 44 can have two loops as shown. The intermediate eyelets 46 and the proximal eyelets 48 can similarly have more than one loop, forming an eyelet. The number of loops forming any eyelet can include approximately 2, 3, 4, 5, 6 or more loops or approximate partial fractions thereof, for example 1.5, 2.5, 3.5, 4.5, 5.5. A preferred method uses approximately two loops to form the eyelets 44, 46, and 48. FIG. 6(A) depicts the approximate configuration of the helical wire 2 while under light tension 72, applied along the longitudinal axis of the helical wire 2. The latch portion 50 of the helical wire 2 can also include multiple loops or any other suitable configuration. Shown is a preferred latch portion 50 configuration having approximately one loop.

Figure 6B:
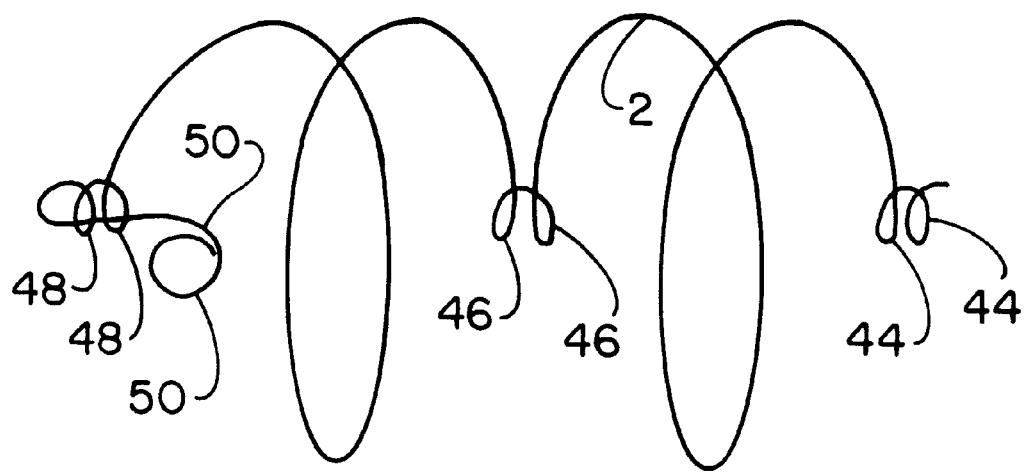

As shown in FIG. 6(B), the helical wire 2 expands into the deployed shape when the longitudinal or linear tension (72, FIG. 6(A)) is removed. The approximate dimensions of the eyelets 44, 46 and 48 are maintained after removal of the longitudinal or linear tension. The latch portion 50 of the helical wire 2 is also approximately maintained after the longitudinal or linear tension is removed.

Figure 7A:
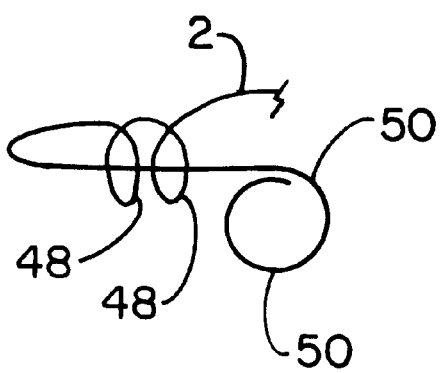
FIGS. 7(A) and (B) show details and alternate configurations of the integral latching and securing means.
Figure 7B:
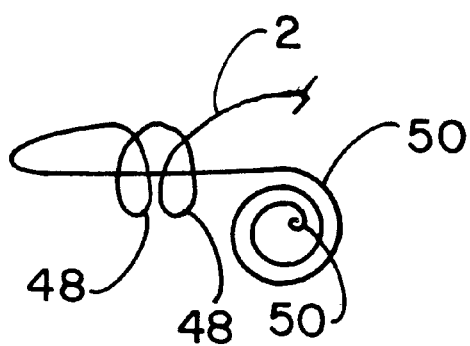

As shown in FIG. 7(A), a preferred embodiment or configuration of the latch portion 50 of the helical shaped wire 2, has at least one loop. The latch portion 50 may also be formed to deploy inward relative to the deployed device or towards the distal eyelet 48 to minimize the protrusion of the latch portion 50 after full deployment. FIG. 7(B) shows an alternate configuration of the latch portion 50 of the helical shaped wire 2, wherein the latch portion has approximately two full rotational loops. In addition the terminal end of the latch portion 50 can be formed into a small loop.

Figure 8A:
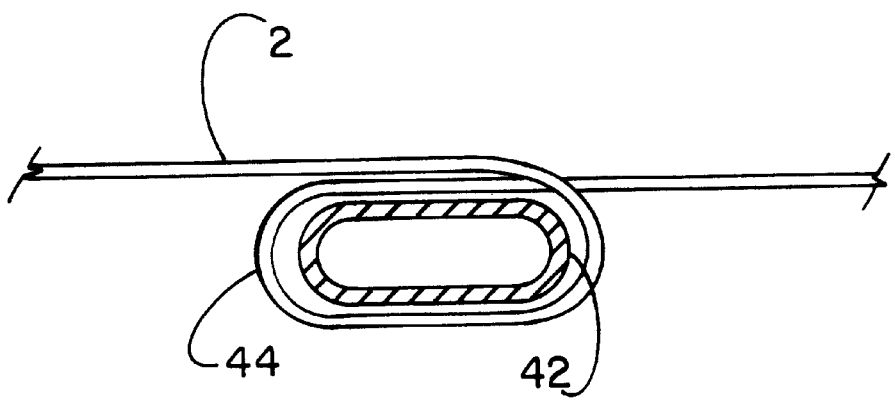
FIGS. 8(A) and (B) show details of a biasing or anti-rotation feature of the wire eyelets and guiding mandrel.

A bias may be applied to the wire to encourage the deployment rotational direction and the longitudinal deployment direction in order to assure a specific deployed configuration. A preferred method of applying this bias is shown in FIGS. 8(A) and (B). The helical shaped wire 2, is formed to create at least one eyelet, for example the proximal eyelet 44. This eyelet is formed into a non-circular or "asymmetric" shape. The guiding mandrel 42 is similarly formed into a corresponding non-circular or "asymmetric" shape. Thus the eyelet engages the mandrel. As the terms "asymmetric and "non-circular" are used herein, each is intended to encompass any non-circular shape that will prevent the eyelet from rotating on a correspondingly shaped guiding mandrel. Such shapes may include without limitation: ovals, squares/rectangles, triangles, and various random shapes, and other shapes that allow linear progression of the eyelet along the mandrel while preventing uncontrolled twisting of the eyelet on the mandrel.

Figure 8B:
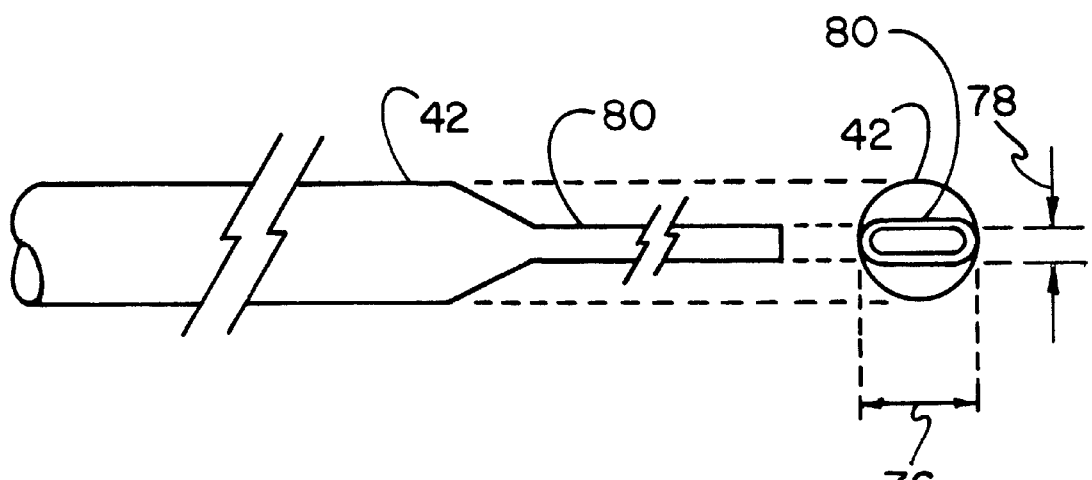

The non-circular or asymmetric form of the eyelet 44, along with the non-circular or asymmetric form of the guiding mandrel 42, prevents rotation or twisting of the mandrel 42 relative to the eyelet 44. The bias applied to the wire is thus an anti-rotation constraint which can assure a specific shape or deployment configuration. FIG. 8(B) shows a side and end view of a preferred guiding mandrel 42 configuration, where the distal end 80 of the guiding mandrel has been formed into a non-circular or asymmetric shape. The asymmetric shape has a width 76 which is substantially greater (hereby defined as more than 10%) than the height 78. In a preferred embodiment all three eyelets (44, 46, 48 FIG. 6(B)) have non-circular or asymmetric forms, such as an oblate rectangle, and a similarly shaped mandrel which allows the eyelets to slide over the mandrel while also preventing relative rotation of the mandrel to the eyelets. With the incorporation of this anti-rotation feature, the eyelets should be, in a preferred embodiment, aligned and not rotated relative to each other after the guiding mandrel has been threaded through the eyelets and the pre-cut mandrel holes, as described in FIGS. 4(A) through (C).

As shown in FIG. 9(A) the eyelets are not rotated and are in a significantly relaxed and unconstrained state while in the deployed configuration. As shown in FIG. 9(B), the helical formed wire 2 is wrapped around the guiding mandrel 42, when the eyelets for example 48 and 46, are forced apart, as during the mandrel threading operation described in FIGS. 4(A) through (C). Thus during the mandrel threading operation, the eyelets should be properly aligned so they are configured as shown in FIG. 9(A) when in the expanded or deployed state. A preferred non-circular or asymmetric tube has a width between about 0.048" to 0.052" (1.22 mm to 1.32 mm), and a height of about 0.023" to 0.027" (0.58 mm to 0.69 mm). Preferred eyelet configurations are sized to allow the eyelets to slide along the asymmetric mandrel yet prevent rotation of the eyelets relative to the mandrel.

As shown in FIG. 10, a low friction coating 82 may, in a preferred embodiment, be applied to the anti-rotation segment of the distal end 80 of the guiding mandrel 42. This coating may be sprayed, vapor coated, or thermally applied. In a preferred embodiment this coating is Paralyne, applied by Specialty Coating Systems, Indianapolis, Ind.

Figure 11A:
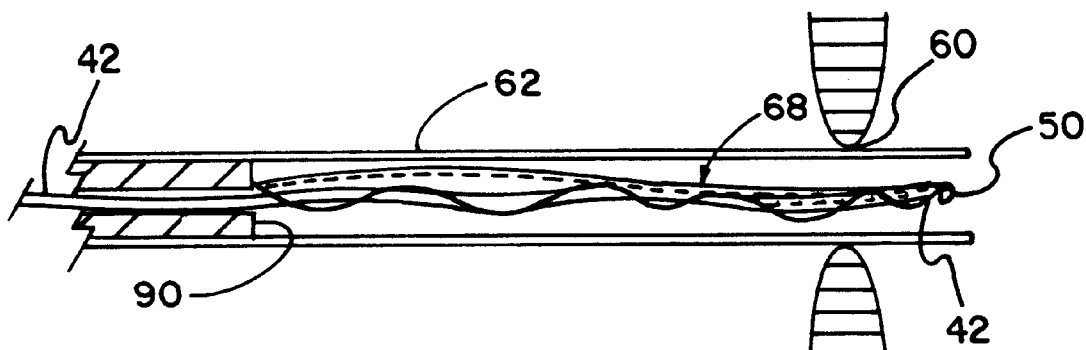
FIGS. 11(A) through (G) show the delivery and deployment sequence of a helical closure device of the present invention along with an integral latch and securing means for sealing member securing and sealing member to sealing member securing. Also shown is a guiding mandrel sealing member central edge converging means.

Deployment of the helical closure device with the latch securing means and the guiding mandrel means is shown in FIGS. 11(A) through (G). As shown in FIG. 11(A), the catheter 62 is aligned to and pushed through the defect 60. The catheter 62 contains the helical closure device 68, a device push tube 90, the guiding mandrel 42 and the latch and securing means 50. The guiding mandrel and the latch and securing portion 50 of the helical shaped wire are then advanced out of the catheter as shown in FIG. 11(A).

Figure 11B:
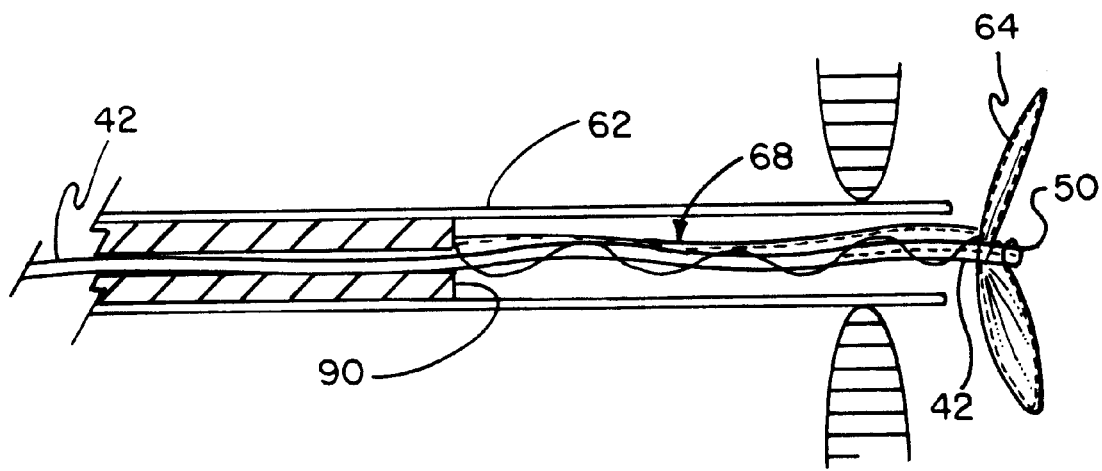

As shown in FIG. 11(B), the pusher tube 90 is then advanced, driving the helical closure device 68 out of the catheter 62. The distal side 64 of the helical closure device 68 then assumes the memory induced shape.

Figure 11C:
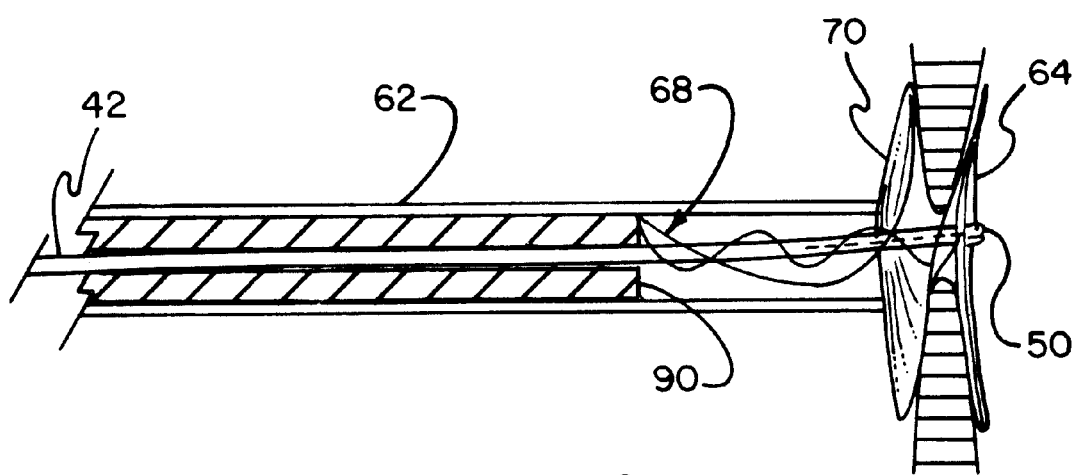

As shown in FIG. 11(C), the catheter 62 is withdrawn away from the defect, forcing the distal side 64 of the closure device 68 against the defect 60. The pusher tube 90 is then advanced toward the defect, driving the helical closure device 68 further out of the catheter 62. The proximal side 70 of the helical closure device 68 then assumes the memory induced shape. The guiding mandrel 42 forces the pre-cut holes 16 (FIG. 2(E)) to become aligned to a common axis and thus provides a sealing member central edge convergence means.

Figure 11D:
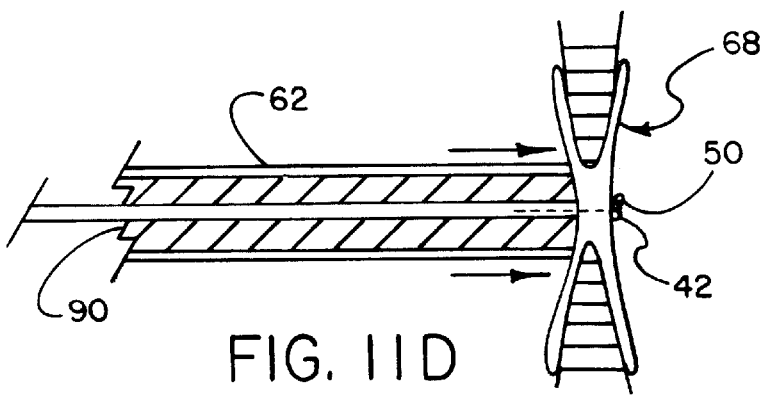
Figure 11E:
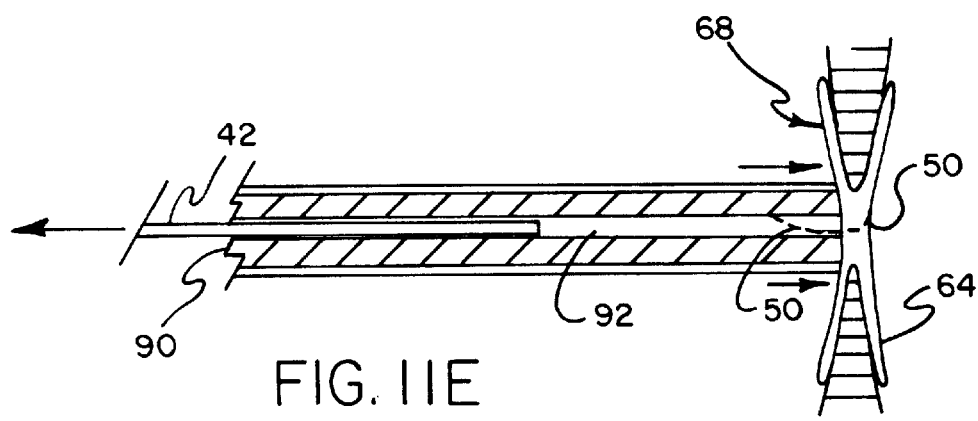

The release of the latch and securing portion 50 is accomplished by advancing the catheter 62 and the pusher tube 90 toward the defect, as shown in FIG. 11(D). As shown in FIG. 11(E), the guiding mandrel 42 can then be drawn away from the helical closure device 68. The pre-cut holes 16 (FIG. 2(E)) are pre-threaded over the guiding mandrel 42 and are thus aligned to a common axis by the guiding mandrel 42. In this configuration the latch and securing portion 50 will spring open towards its memory induced shape, and conform the inner diameter 92 of the pusher tube 90.

Figure 11F:
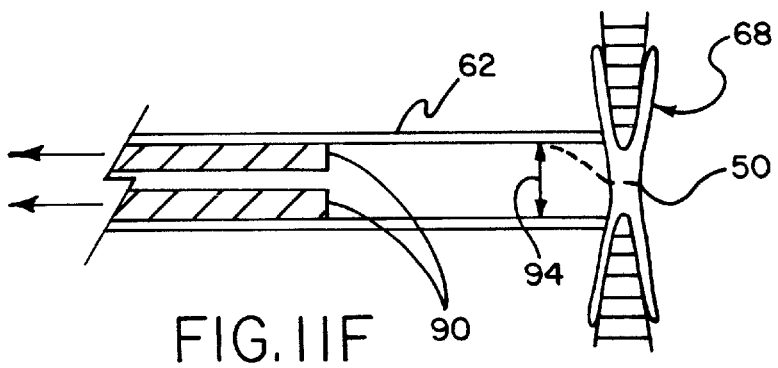

As shown in FIG. 11(F), the pusher tube 90 may then be withdrawn away from the helical closure device 68, allowing the latch and securing portion 50 to further spring open towards the unconstrained memory induced shape and conform to the inner diameter 94 of the catheter 62.

Figure 11G:
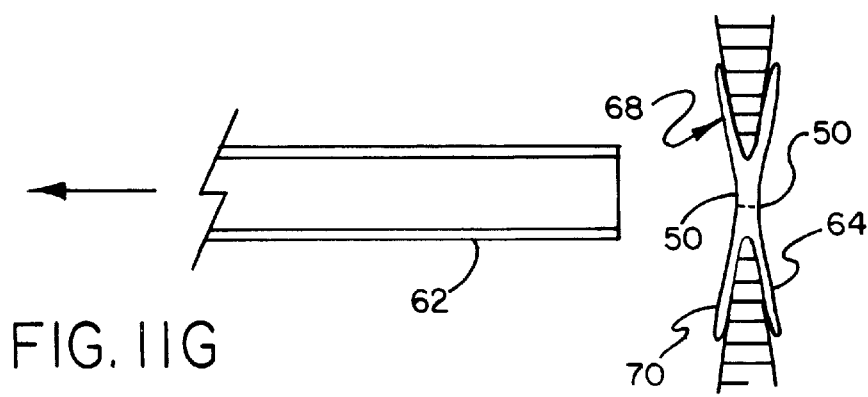

As shown in FIG. 11(G), the catheter 62 can then be withdrawn from the helical closure device, fully releasing the latch and securing portion 50, which will then spring open to its memory induced shape. The latch and securing portion 50 now provides a means to secure the distal side membrane 64 to the proximal side membrane 70 of the helical closure device 68 and also provide a sealing member securing means. Alternate methods for deploying the latch include withdrawing the guiding mandrel 42 and the catheter 62 simultaneously away from the helical closure device 68, or withdrawing the guiding mandrel 42, the pusher tube 90 and the catheter 62 simultaneously away from the helical closure device 68.

Figure 12A:
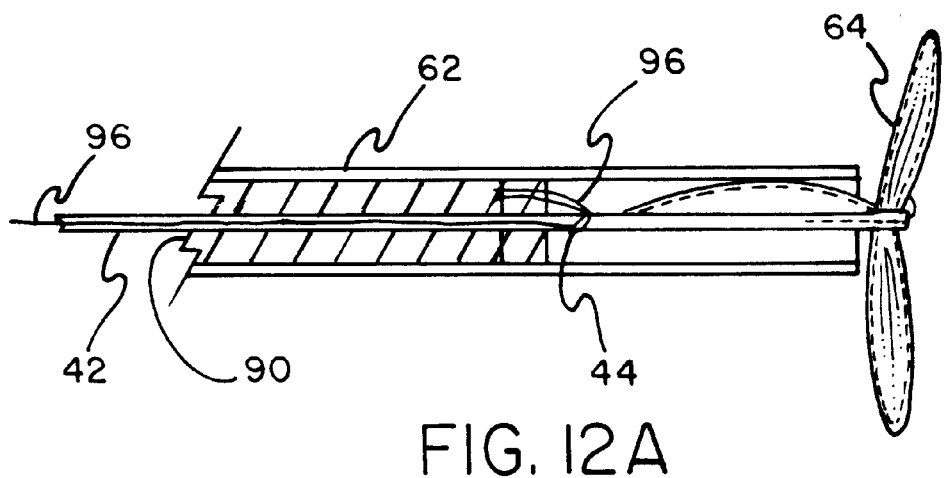
FIGS. 12(A) through (C) show a suture retrieval means.
Figure 12B:
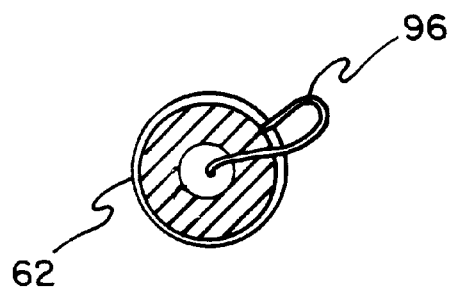
Figure 12C:
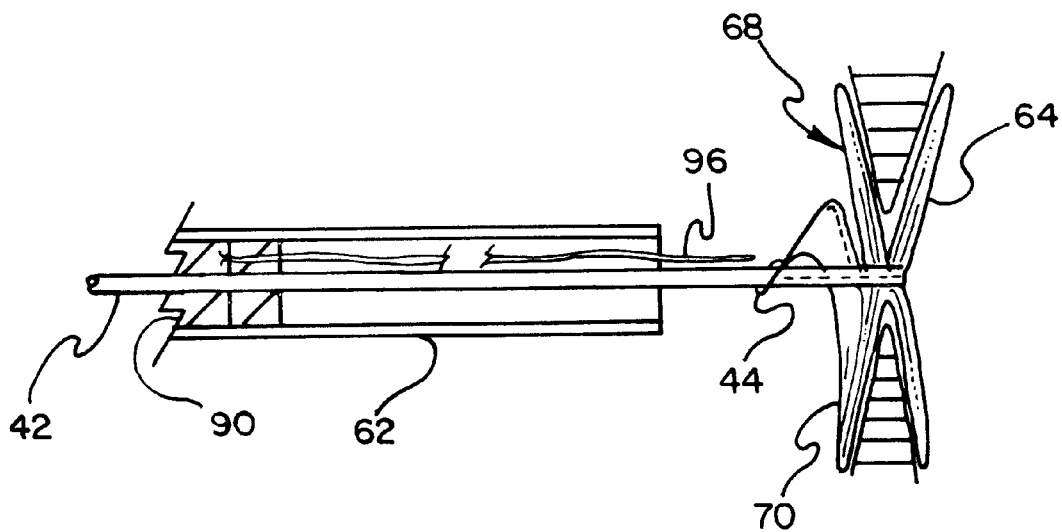

A means for allowing device retrieval during the deployment is desirable. A device retrieval means is defined as a means to allow the defect closure device to be reinserted into the delivery catheter after partial deployment of the defect closure device. If the closure device is inadvertently mispositioned during deployment, a suture with one end embedded or attached to the pusher tube, allows retrieval of the partially deployed device. Thus the device can be withdrawn back into the delivery catheter and redeployed to correct the positioning error FIGS. 12(A) through (C) show a preferred embodiment of a suture retrieval means. As shown in FIG. 12(A), a suture 96 is pre-threaded through the proximal eyelet 44. One end of the suture 96 is embedded or attached to the push tube 90 and the other end of the suture 96 is pre-threaded through the proximal eyelet 44 and pre-threaded through the inside lumen of the push tube 90. The suture 96 is pre-threaded or routed between the outside of the guiding mandrel 42 and the inside lumen of the push tube 90 and extends out of the proximal end of the delivery catheter 62. By tensioning the exposed end of the suture at the proximal end of the delivery catheter, the closure device can be drawn back into the delivery catheter 62 if re-deployment is required. As shown in FIG. 12(B), the push tube 90 has the suture 96 attached or embedded into the push tube 90. As shown in FIG. 12(C), deployment of the closure device 68 can be completed by releasing the suture from the proximal end of the delivery catheter 62 and as the catheter 62 is withdrawn, the suture 96 is allowed to slip through the proximal eyelet 44, thereby releasing the closure device 68.

Figure 13:
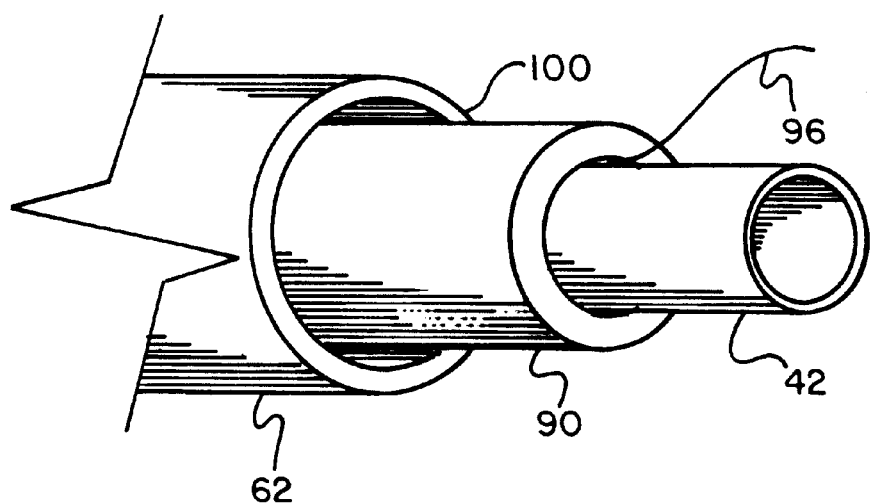
FIG. 13 shows the proximal end of the delivery catheter with the coaxial arrangement of the guiding mandrel, the push tube and the delivery catheter. Also shown is the proximal end of the retrieval suture.

Shown in FIG. 13 is the proximal end 100 of the delivery catheter 62. The guiding mandrel 42 and the push tube 90 are configured coaxially within the delivery catheter 62. The proximal end of the retrieval suture 96 is routed between the outside of the guiding mandrel 42 and the inside lumen of the push tube 90 and is removably secured to the push tube 90. In a preferred embodiment, the suture 96 can be removably secured to the push tube 90 by a pressure fit cap that pinches and holds the suture to the outside diameter of the push tube. To complete the device delivery, the pressure fit cap is removed, thereby freeing the suture 96 and allowing the suture to slip through the push tube lumen and through the proximal eyelet of the helical formed wire, which fully releases the device.

To allow the guiding of the delivery catheter through a defect without the need of a guide wire, the distal end of the delivery catheter has an articulated tip.

Figure 14A:
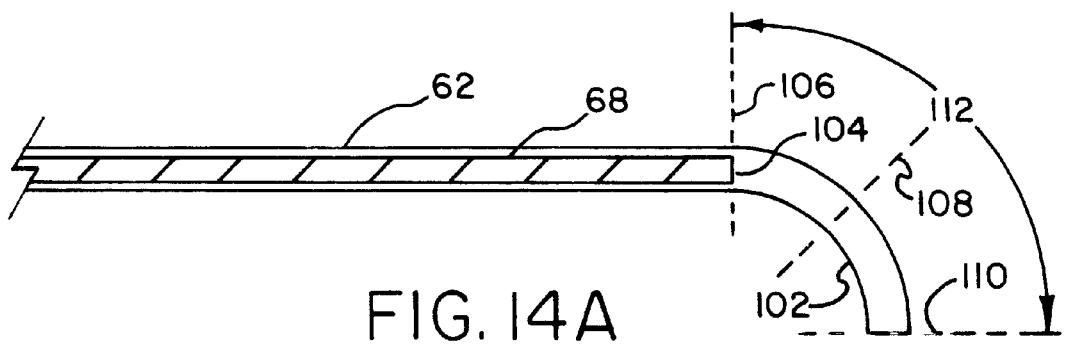
FIGS. 14(A) through (C) show the articulating tip of the distal end of the delivery catheter.
Figure 14B:
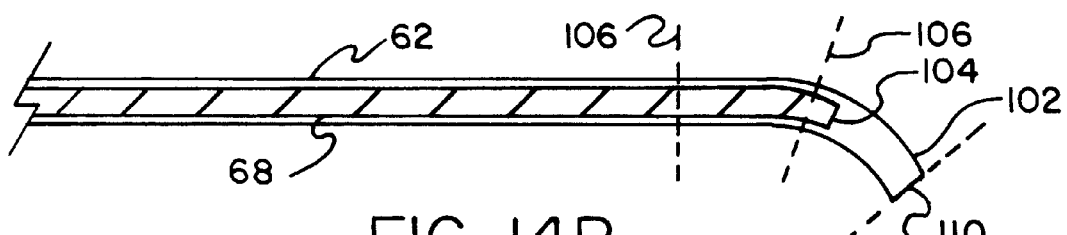
Figure 14C:
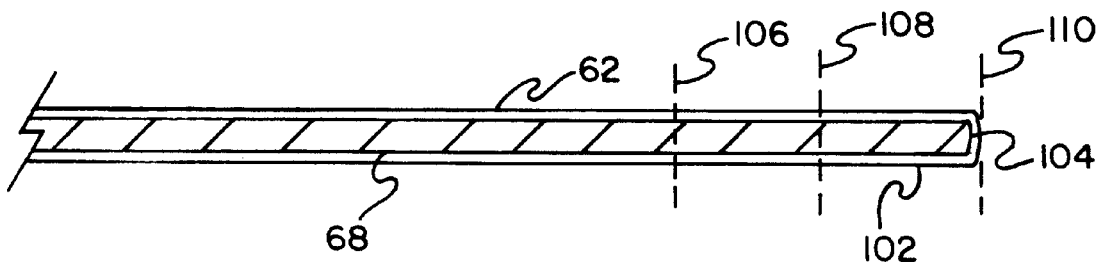

This hooked tip facilitates "steering" of the delivery system through passageways or "hooked" in a _____, much like a bent tip on a guidewire catheter. As shown in FIGS. 14(A) through (C), the distal end of the catheter 62 has an articulated tip 102. As shown in FIG. 14(A), the distal end of the catheter assumes a bend or angle 112 of approximately 60 to 90 degrees when in the relaxed or unconstrained state. In this state, the distal end 104 of the device 68 is at the proximal position 106. Referring to FIG. 14(B), as the distal end 104 of the device 68 is advanced towards the medial position 108, the articulated tip 102 bends, approximating less of an angle. Shown is an approximate starting angle of 90 degrees (FIG. 14(A)) transitioning to an approximate angle of 45 degrees, as shown in FIG. 14(B). As the distal end 104 of the device 68 is further advanced to the distal position 110, the articulated tip assumes an approximate linear or straight configuration. Thus the distal tip is adapted to assume at least two different positions, a bent guiding position as shown in FIG. 14(A), and a straightened device deployment position as shown in FIG. 14(C). The distal tip actuates from the guiding position to the device deployment position when the defect closure device is moved through the distal tip. It should be appreciated that the tip is able to assume a variety of bent configurations between these two extreme positions simply by partially advancing or withdrawing the devices within the tip.

The catheter tube comprises a flexible material adapted to flex so as to straighten the hooked end as shown in FIG. 14(C) when a device is deployed through the tube. In a preferred embodiment, the delivery catheter is constructed from a wire braiding support with approximately 40 crossovers per inch, coated with hot melt Pebax, which can be procured from Elf Atochem North American, Inc., Philadelphia, Pa. Other stiffening materials may be substituted for the Pebax, such as FEP or other suitable materials. Alternatively, the catheter tube itself may be bowel from a material that will accept a heat-set or molded or other formed bend. The dimensions of the wire braiding are selected for the specific catheter size. Other materials may be substituted for the wire braiding, for example polymer fibers or filaments may be used for the catheter support. The catheter support can also be in the form of a spiral or coil. The support may be eliminated providing the catheter has adequate mechanical and flexural properties.

The pre-bent or hooked portion of the distal tip is formed by constraining the distal tip in the bent or hooked configuration as the hot melt Pebax is heated to its approximate melting or reflow temperture. The catheter is then allowed to cool while remaining in the constrained state. The articulated portion is, in a preferred embodiment, approximately 2.4" (61 mm) long and forms an approximate 90 degree angle. Radio-opaque rings, or tips may be incorporated into the distal catheter tip by forming a mixture of approximately 80% tungsten fine powder and 20% Pebax. The metal loaded mixture is then melted and molded onto the distal catheter tip. To lower the surface friction in the push tube inner lumen, a densified, thin wall PTFE liner may be optionally incorporated onto the inner lumen. In a preferred embodiment, the suture may be affixed to the push tube by melting the hot melt Pebax around the suture, thereby embedding the suture into the push tube wall.

Figure 15B:
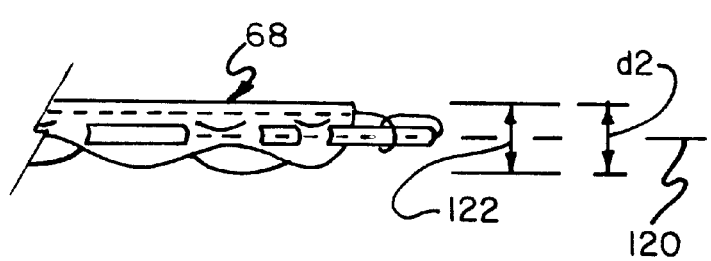
FIG. 15(B) shows a side view of the closure device, in a fully collapsed or small diameter state.
Figure 15A:
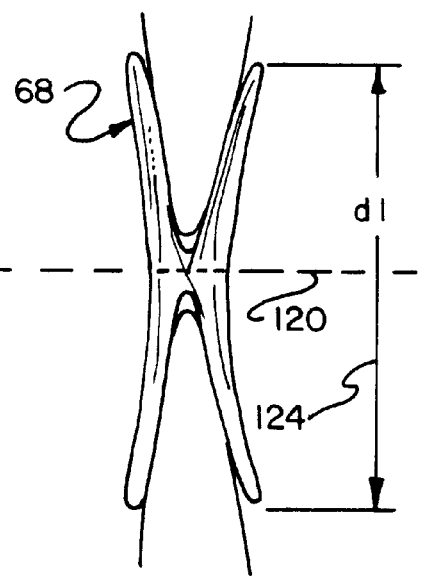
FIG. 15(A) shows a side view of a closure device of the present invention in a deployed or large diameter state.

FIG. 15(A) shows a side view of a closure device 68, with a longitudinal axis 120, in the deployed or large diameter state 124 having a diameter $d_1$.

FIG. 15(B) shows a side view of a closure device 68, with a longitudinal axis 120, in the fully collapsed or small diameter state 122 having a diameter $d_2$, where $d_2$ is less than $d_1$, the ratio of $d_1:d_2$ being less than about 50:1, depending on the final deployed diameter $d_1$ of the device. The ratio of $d_1:d_2$ should be between about 5:1 and about 50:1, with a ratio of about 5:1 to about 50:1 being preferred (such as, 5:1, 7:1, 8:1, 9:1, 10:1, 12:1, 15:1, 20:1, 25:1, 30:1, 35:1, 40:1, 45:1.) Once in the collapsed state, the device can be inserted along the longitudinal axis 120 into a delivery tube or catheter 62. Thus the device has a compressed insertion configuration and an enlarged deployed configuration.

Although, the present invention is preferred to close body defects like atrial septal defects and ventricular septal defects, it can be used in other applications where the undesired communication or passage in the body exists. One specific example is Patent Ductus Arteriosis (PDA). PDA is a vessel which shunts aorta and pulmonary artery. This shunt is supposed to close immediately after childbirth. However, in certain congenital disease conditions, this vessel stays open after childbirth and hence leads to subsequent complications. It is desired to have a catheter based or thoroscopic device to block PDA. The present invention can be used for the PDA closure. Similarly, it can be used to block the flow in any tubular structure in the body such as fallopian tubes, arteriovenous fistula, etc.

In this respect, it should be appreciated that the present invention can be introduced in a wide variety of manners, including by merely using a tube ("catheter"), through thoracoscopic delivery, or other means. For small applications, it may be desirable to use pediatric sized catheters.

It should be appreciated from the foregoing description that an important benefit of the present invention, particularly the helically deployed embodiment, is that it can be restrained to a very compact insertion diameter and yet still fully expand to assume a full barrier to cover or seal a wall defect. This dramatic change in size is achieved by the ability of the elastic support of the present invention to assume a substantially elongated configuration in its insertion configuration and then automatically bend into another periphery of the closure device in its deployed configuration.

As the term "substantially elongated" is used herein, it is intended to encompass any orientation of the elastic support that stretches the support out longitudinally within a delivery tube. Preferably a "substantially elongated" support assumes nearly a straight line within the delivery tube; however, the term is intended to encompass any longitudinally disposed orientation, such as a stretched wire having one or more loops or kinks therein or even a support that may include two or more lengths of wire along its length.

The advantage of this construction is that the closure device can be compressed into very small tubes for delivery into tightly confined spaces. For instance, the closure device of the present invention will readily compact into a 9 French (F) catheter tube, and even much smaller tubes such as 8F, 7.5F, 7F, 6.5F, 6F, 5.5F, 5F, 4.5F, 4F, 3.5F, 3F, 2.5F, 2F and even smaller.

A further advantage of this construction of the closure device of the present invention is that the device remains quite flexible in its compacted, insertion configuration. This is particularly true where the elastic support comprises only a single length of wire in its compacted state. This high degree of flexibility contributes to ease of manipulation of the device of the present invention, again assisting in deployment in tight confines.

Another way to express the advantages of the present invention is in the length of the insertion configuration of the present invention relative to the total length of the periphery of the device in its deployed configuration.

This ratio is generally about 0.7 or more, and may include ratios of 0.8, 0.9, 1.0, 1.1, 1.2, 1.3, 1.4, 1.5 or more. Preferably the ratio is 0.7 or more.

Although the invention has been described in conjunction with specific embodiments, it is evident that many alternatives and variations will be apparent to those skilled in the art in light of the foregoing description and annexed drawings. Accordingly, the invention is intended to embrace all of the alternatives and variations that fall within the spirit and scope of the appended claims.

What is claimed is:

1. A sealing device comprising:
   an elastic member forming a periphery and supporting a sealing membrane;
   the elastic member having at least one eyelet; and
   a guiding mandrel;
   wherein the eyelet is adapted to slide over the guiding mandrel.

2. The sealing device according to claim 1, wherein the periphery is helical shaped.

3. The sealing device according to claim 1, wherein the at least one eyelet is integrally formed from the elastic member.

4. The sealing device according to claim 1 wherein the eyelet and guiding mandrel are adapted to prevent eyelet rotation relative to the guiding mandrel.

5. The sealing device according to claim 4, wherein the eyelet and guiding mandrel are non-circular in shape as to prevent eyelet rotation on the mandrel.

6. The sealing device according to claim 1 wherein the guiding mandrel comprises a polymer.

7. The sealing device according to claim 1 wherein the guiding mandrel comprises a metal.

8. The sealing device according to claim 7, wherein the metal is nitinol.

9. The sealing device according to claim 1, wherein the elastic support is a wire.

10. The sealing device according to claim 9, wherein the wire has a non-circular form.

11. The sealing device according to claim 9, wherein the wire is super-elastic.

12. The sealing device according to claim 9, wherein the wire has shape memory.

13. The sealing device according to claim 9, wherein the wire is nitinol.

14. The sealing device according to claim 1, wherein the sealing membrane is formed from a polymer.

15. The sealing device according to claim 14, wherein the polymer is a fluoropolymer.

16. The sealing device according to claim 15, wherein the fluoropolymer is polytetrafluoroethylene.

17. The sealing device according to claim 16, wherein the polytetrafluoroethylene is expanded polytetrafluoroethylene having a node and fibril structure.

18. A sealing device comprising:
   an elastic member forming a periphery and supporting a sealing membrane;
   the elastic member having at least one eyelet;
   wherein the periphery is helical shaped.

19. The sealing device according to claim 18 wherein the at least one eyelet is integrally formed from the elastic member.

20. The sealing device according to claim 18 which further includes a guiding mandrel and the eyelet is adapted to slide over the guiding mandrel.

21. The sealing device according to claim 20 wherein the eyelet and guiding mandrel are adapted to prevent eyelet rotation relative to the guiding mandrel.

22. The sealing device according to claim 21 wherein the eyelet and guiding mandrel are non-circular in shape as to prevent eyelet rotation on the mandrel.

23. The sealing device according to claim 20 wherein the guiding mandrel comprises a polymer.

24. The sealing device according to claim 20 wherein the guiding mandrel comprises a metal.

25. The sealing device according to claim 24 wherein the metal comprises nitinol.

26. The sealing device according to claim 18 wherein the elastic membrane is a wire.

27. The sealing device according to claim 26 wherein the wire has a non-circular form.

28. The sealing device according to claim 26 wherein the wire is nitinol.

29. The sealing device according to claim 26 wherein the sealing membrane is formed from a polymer.

30. The sealing device according to claim 29 wherein the polymer is a fluoropolymer.

* * * * *